(12) United States Patent
Russo et al.

(10) Patent No.: US 9,126,988 B2
(45) Date of Patent: Sep. 8, 2015

(54) INTERMEDIATE FOR PREPARING A CATECHOL-O-METHYLTRANSFERASE INHIBITOR

(71) Applicant: BIAL-PORTELA & CA, S.A., S. Mamede do Coronado (PT)

(72) Inventors: Domenico Russo, S. Mamede do Coronado (PT); Laszlo Erno Kiss, S. Mamede do Coronado (PT); Jorge Bruno Reis Wahnon, S. Mamede do Coronado (PT); David Alexander Learmonth, Alfena (PT); Tibor Eszenyi, Tiszalok (HU); Axel Zimmermann, Kirkel-Altstadt (DE); Bjoern Schlummer, Leverkusen (DE); Michael Kreis, Leverkusen (DE); Klaus Reiter, Linz (AT)

(73) Assignee: BIAL—PORTELA & CA, S.A., S. Mamede do Coronado (PT)

( * ) Notice: Subject to any disclaimer, the term of this patent is extended or adjusted under 35 U.S.C. 154(b) by 0 days.

(21) Appl. No.: 14/365,265

(22) PCT Filed: Dec. 12, 2012

(86) PCT No.: PCT/PT2012/000048
§ 371 (c)(1),
(2) Date: Jun. 13, 2014

(87) PCT Pub. No.: WO2013/089573
PCT Pub. Date: Jun. 20, 2013

(65) Prior Publication Data
US 2014/0350057 A1 Nov. 27, 2014

Related U.S. Application Data

(60) Provisional application No. 61/718,589, filed on Oct. 25, 2012, provisional application No. 61/593,625, filed on Feb. 1, 2012, provisional application No. 61/570,141, filed on Dec. 13, 2011.

(30) Foreign Application Priority Data

Dec. 13, 2011 (GB) .................................... 1121413.7
Feb. 1, 2012 (GB) .................................... 1201758.8

(51) Int. Cl.
*C07D 413/04* (2006.01)

(52) U.S. Cl.
CPC .................................... *C07D 413/04* (2013.01)

(58) Field of Classification Search
None
See application file for complete search history.

(56) References Cited

U.S. PATENT DOCUMENTS

| 8,168,793 | B2 | 5/2012 | Learmonth et al. | |
|---|---|---|---|---|
| 8,524,746 | B2 | 9/2013 | Learmonth et al. | |
| 8,536,203 | B2 | 9/2013 | Learmonth et al. | |
| 8,907,099 | B2 * | 12/2014 | Learmonth et al. | 546/269.4 |
| 2010/0168113 | A1 | 7/2010 | Learmonth et al. | |
| 2011/0301204 | A1 | 12/2011 | de Almeida et al. | |
| 2012/0196904 | A1 | 8/2012 | Learmonth et al. | |
| 2013/0324578 | A1 | 12/2013 | Soares Da Silva et al. | |
| 2013/0331416 | A1 | 12/2013 | Learmonth et al. | |
| 2014/0024682 | A1 | 1/2014 | Learmonth et al. | |
| 2014/0045900 | A1 | 2/2014 | Soares Da Silva et al. | |

FOREIGN PATENT DOCUMENTS

| WO | 2007/013830 A1 | 2/2007 |
|---|---|---|
| WO | 2008/094053 A1 | 8/2008 |
| WO | 2012/107708 A1 | 8/2012 |

OTHER PUBLICATIONS

"[1,2,4]-oxadazolyl nitrocatechol derivatives" IP. COM Journal, IP.COM Inc., West Henrietta, NY, US, May 3, 2012. XP013150541.
Kiss, L E et al., "Discovery of a long-acting, peripherally selective inhibitor of a catechol-O-methyltransferase" Journal of Medicinal Chemistry, American Chemical Society, US, vol. 53, No. 8, Apr. 22, 2010, pp. 3396-3411. XP002594266.
Rasenack, N. et al., "Micron-size drug particles: common and novel micronization techniques", Pharmaceutical Development and Technology, New York, NY, US, vol. 9, No. 1., Jan. 1, 2004, pp. 1-13. XP009055393.

\* cited by examiner

*Primary Examiner* — Heidi Reese
(74) *Attorney, Agent, or Firm* — McCarter & English, LLP; Steven G. Davis; Wei Song

(57) ABSTRACT

There is disclosed a methylated intermediate which may be demethylated to provide an inhibitor of catechol-O-methyltransferase useful in the treatment of Parkinson's disease. Also disclosed are methods of making and using said intermediate.

30 Claims, 6 Drawing Sheets

INTERMEDIATE FOR PREPARING A CATECHOL-O-METHYLTRANSFERASE INHIBITOR

RELATED APPLICATIONS

This application is a 35 U.S.C. §371 national stage filing of International Application No. PCT/PT2012/000048, filed Dec. 12, 2012, which claims priority under 35 U.S.C. §365 to Great Britain Patent Application No. 1201758.8, filed on Feb. 1, 2012; Great Britain Patent Application No. 1121413.7, filed on Dec. 13, 2011; U.S. Provisional Application No. 61/718,589, filed on Oct. 25, 2012; U.S. Provisional Application No. 61/593,625, filed on Feb. 1, 2012; and U.S. Provisional Patent Application No. 61/570,141, filed on Dec. 13, 2011. The entire contents of each of the aforementioned applications are incorporated herein by reference.

FIELD OF THE INVENTION

The present invention relates to a novel compound and to processes which employ it in the preparation of a catechol-O-methyltransferase inhibitor. In particular this invention relates to 5-[3-(2,5-dichloro-4,6-dimethyl-1-oxy-pyridin-3-yl)-[1,2,4]oxadiazol-5-yl]-2-hydroxy-3-methoxy-1-nitrobenzene which can be used in the process for the preparation of 5-[3-(2,5-dichloro-4,6-dimethyl-1-oxy-pyridin-3-yl)-[1,2,4]oxadiazol-5-yl]-3-nitrobenzene-1,2-diol.

BACKGROUND TO THE INVENTION

A preferred method of treatment of Parkinson's disease is the administration of a combination of levodopa and a peripherally selective aromatic amino acid decarboxylase inhibitor (AADCI) together with a catechol-O-methyltransferase (COMT) inhibitor. The currently employed COMT inhibitors are tolcapone and entacapone. However, some authorities believe that each of these COMT inhibitors have residual problems relating to pharmacokinetic or pharmacodynamic properties, or to clinical efficiency or safety. Hence, not all patients get most benefit from their levodopa/AADCI/COMT inhibitor therapy.

Favoured new COMT inhibitors were disclosed in L. E. Kiss et al, J. Med. Chem., 2010, 53, 3396-3411 (D1), WO 2007/013830 (D2) and WO 2007/117165 (D3) which are believed to have particularly desirable properties so that patients can benefit from enhanced therapy.

D1, D2 and D3 also disclosed methods of preparing the new COMT inhibitors. Those processes, although effective, would benefit from an increase in yields. Other benefits which would be appropriate include those selected from reduction in number of process steps, reduction in number of unit operations, reduction of cycle-times, increased space yield, increased safety, easier to handle reagents/reactants and/or increase in purity of the COMT inhibitor, especially when manufacture of larger quantities are envisaged. A process has now been discovered that proceeds via a new intermediate which is suitable for manufacture of commercially useful quantities of a particularly apt COMT inhibitor in good yield. Additional benefits occur such as those selected from a reduced number of process steps and number of unit operations, reduced cycle-times, increased space yield, increased safety, with easier to handle reagents/reactants, improved impurity profile and/or good purity.

BRIEF DESCRIPTION OF THE INVENTION

The present invention in one aspect provides 5-[3-(2,5-dichloro-4,6-dimethyl-1-oxy-pyridin-3-yl)-[1,2,4]oxadiazol-5-yl]-2-hydroxy-3-methoxy-1-nitrobenzene and salts thereof, that is the compound of the formula (I):

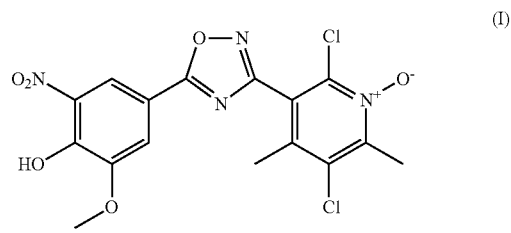 [SMILES: COc1cc(-c2nc(-c3c(C)c(Cl)c(C)[n+]([O-])c3Cl)no2)cc([N+](=O)[O-])c1O]

(I)

and salts thereof.

Most aptly the compound of formula (I) is unsalted. However, salts of the hydroxy group with metal ions such as the alkali or alkaline earth metals, particularly the sodium and potassium salts are provided as well as those of highly basic organic compounds such as guanidine or the like.

Particularly suitably the compound of formula (I) or its salt is provided in a form suitable for use as a chemical intermediate. This may be, for example, in a form at least 50% pure, in crystalline form, in solid form or in an organic solvent or the like.

The compound of formula (I) is useful as an intermediate in the preparation of 5-[3-(2,5-dichloro-4,6-dimethyl-1-oxy-pyridin-3-yl)-[1,2,4]oxadiazol-5-yl]-3-nitrobenzene-1,2-diol i.e. the compound of formula (II):

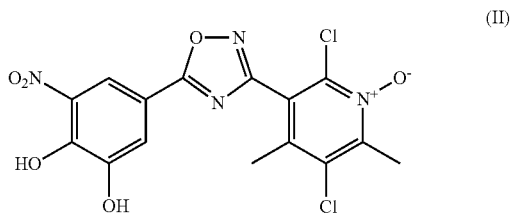 [SMILES: Cc1c(Cl)c(C)[n+]([O-])c(Cl)c1-c1noc(-c2cc(O)c(O)c([N+](=O)[O-])c2)n1]

(II)

The compound of formula (II) may also be referred to as opicapone or 2,5-dichloro-3-(5-(3,4-dihydroxy-5-nitrophenyl)-[1,2,4]-oxadiazole-3-yl)-4,6-dimethylpyridine-1-oxide. Opicapone has been found to be more potent than tolcapone in inhibiting liver COMT both at 3 hours and 6 hours post oral administration to rats [ED$_{50}$ in mg/kg, opicapone 0.87 at 3 hours and 1.12 at 6 hours as compared to tolcapone 1.28 at 3 hours and 2.08 at 6 hours]. Opicapone at a dose of 3 mg/kg was found to be more effective at inhibiting rat liver COMT with nearly complete inhibition occurring 2 to 6 hours post oral administration with only about 90% of enzyme activity recovered after 72 hours while tolcapone provided shorter duration of activity with about 84% recovery after only 9 hours. Both opicapone and tolcapone inhibit human recombinant S-COMT but opicapone has an inhibitory constant of 16 pM being 10 fold lower than that for tolcapone. With respect to the desirable property of avoiding inhibition of COMT in the brain, opicapone following oral administration to the rat was found to be devoid of effect whereas tolcapone inhibited about 50% of enzyme activity over a period of 8 hours post administration.

In a further aspect the invention provides a process for the preparation of the compound of the formula (II) as set forth above or a salt thereof which comprises the demethylation of a compound of the formula (I) as set forth above or a salt thereof. In one embodiment, the process does not require compound of the formula (I) to be dried for the subsequent demethylation reaction, i.e. compound of the formula (I) may be wet with toluene. Typically, the amount of toluene in compound of the formula (I) is in the range 1% to 60% w/w. This is advantageous as it improves the process time and safety. In another embodiment, the process does not require the compound of the formula (II) to be slurried in EtOH. This is advantageous as it improves the process cycle-time.

Most aptly the process is adapted to the preparation of a compound of the formula (II) but salts thereof may be prepared, for example an alkali metal or alkaline earth metal salt, preferably the sodium or potassium salt, or a salt of a strongly basic organic compound such as a guanidine.

The O-demethylation reaction may be effected by reaction with a demethylating reagent. A suitable demethylating reagent is a Lewis acid in the presence of appropriate base, for example, aluminium chloride ($AlCl_3$) and pyridine. The demethylation will generally be performed at a moderately elevated temperature, preferably between 45° C.-70° C., more preferably between 55° C.-65° C.

The compound of the formula (II) prepared by this process can be sufficiently pure for use in a pharmaceutical composition for use in the treatment of Parkinson's disease as hereinbefore indicated. The thus prepared compound of formula (II) may be ball milled or otherwise provided in microparticulate form, for example micronized through jet mills (MC JETMILL®). Thus, in a further aspect of the invention provides a pharmaceutical composition which comprises a compound of formula (II) in microparticulate form for use in the treatment of Parkinson's disease by oral administration.

It is a particular advantage of the present process that the product of the reaction of the compounds of formulas (IV) and (V) obtained after precipitation with ethanol may be employed without the need for isolation of crude compound of formula (III) as the work-up procedure allows the isolation of compound of formula (III) with a purity not less than 95% (HPLC), preferably not less than 96% and ready to use in the next stage of the synthesis. Another advantage of the present process is the optional ability to omit the isolation of any intermediate compounds of the reaction of the compounds of formulas (IV) and (V).

In one embodiment, the acyl chloride may be prepared by the reaction of the compound of formula (VI):

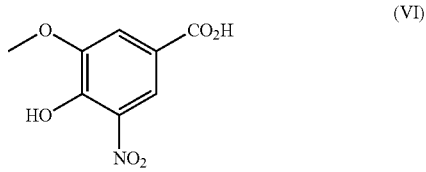

(VI)

with $SOCl_2$ in dioxane at 75° C.-85° C. The use of dioxane in this stage facilitates ease of use in subsequent reactions, for example if it occurs in a solvent system containing dioxane (no need for solvent swap before proceeding with the next step), allows a higher space yield, higher process output, requires less reaction vessels, shorter reaction times, improved solubility of reactants (homogeneous reaction solutions mixture instead of a slurry) and avoids the use of DMF (increased purity).

In another embodiment, the reaction of compound of formula (VI) with $SOCl_2$ is performed in DCM in the presence of a catalytic amount of DMF at 35-50° C., preferably at reflux temperature.

When preparing the compound of formula (II) in a form for use in a pharmaceutical composition, it may be recrystallized from propan-2-ol and formic acid and thereafter ball milled or micronized through spiral jet mills to provide particles of the desired size for good oral bioavailability and/or suitable properties (e.g. suitable particle size) for the preparation of a pharmaceutical composition.

BRIEF DESCRIPTION OF THE FIGURES

Acronyms List

DMF—Dimethylformamide
$SOCl_2$—Thionyl Chloride
MeOH—Methanol
THF—Tetrahydrofuran
DMAc—Dimethyl acetamide
TFAA—Trifluoroacetic acid anhydride
IPA—Isopropoanol
$HNO_3$—Nitric acid
DCM—Dichloromethane
EtOH—Ethanol
HCl—Hydrochloric acid
UHP—Urea Hydrogen Peroxide
$AlCl_3$—Aluminium trichloride
NMP—N-methylpyrolidone
$POCl_3$—Phosphoryl chloride
$(CH_3)_4NCl$—Tetramethylammonium chloride FIG. 1. Process to prepare compound of formula (II) using compound of formula (I) as an intermediate according to one embodiment of the invention.

1. nitric acid 65%, acetic acid, 10-20° C., recrystallization; 2. $SOCl_2$, DMF (catalytic), 50° C.; 3. 50% hydroxylamine in water, catalytic amount of 1,10-phenantroline hydrate, MeOH, 75-80° C.; 4. THF, DMAc, pyridine, 110-120° C.; 5. TFAA, DCM, UHP, 10-20° C.; 5a. solvent swap from DCM to acetonitrile; 5b. crystallization from toluene/formic acid; 6. aluminium chloride, pyridine, N-methylpyrrolidone; 6a. Ethanol reslurry; 6b. Re-crystallization from IPA/formic acid.

Figure 1:
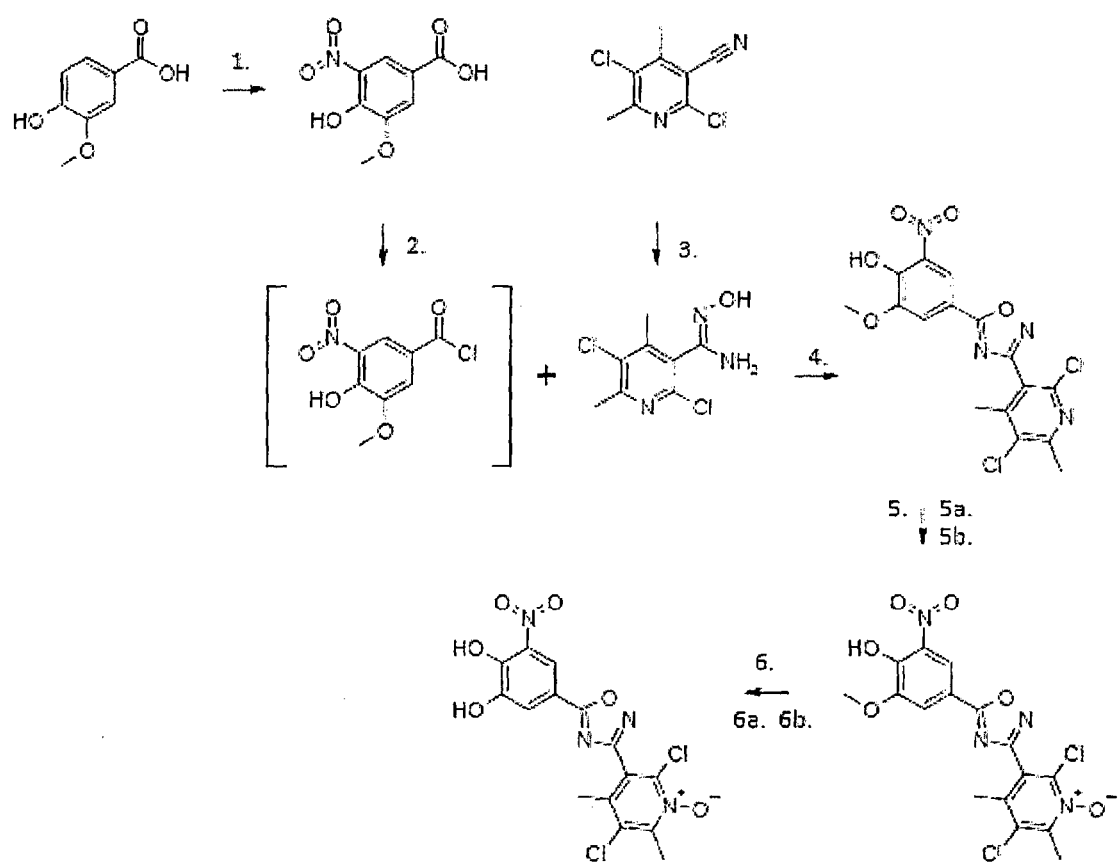
Figure 2:
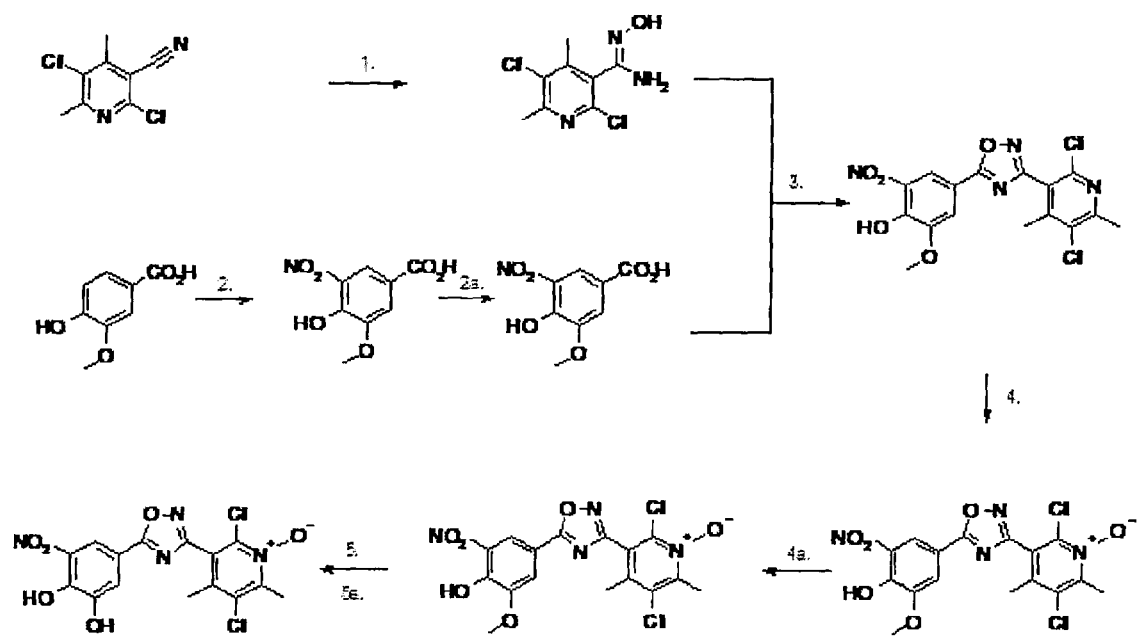

FIG. 2. Process to prepare compound of formula (II) using compound of formula (I) as an intermediate according to one embodiment of the invention.

1. 50% $NH_2OH$ in water, catalytic amount of 1,10-phenantroline hydrate MeOH; 2. 65% $HNO_3$, acetic acid, 2a. Re-crystallization from acetic acid; 3. $SOCl_2$, DCM, DMF (catalytic), solvent switch from DCM to THF, addition of acid chloride to amidoxime in DMAc, addition of pyridine, heat to 110° C.; Quench on aq. HCl and DCM; crystallization from DCM/EtOH; 4. DCM, UHP, TFAA, solvent switch from DCM to toluene/formic acid; crystallization from toluene/formic acid; 4a. Re-crystallization from formic acid/toluene; 5. $AlCl_3$, NMP, pyridine, the compound of formula (II) is precipitated and isolated by addition of diluted HCl; 5a. Re-crystallization from IPA/formic acid.

Figure 3:
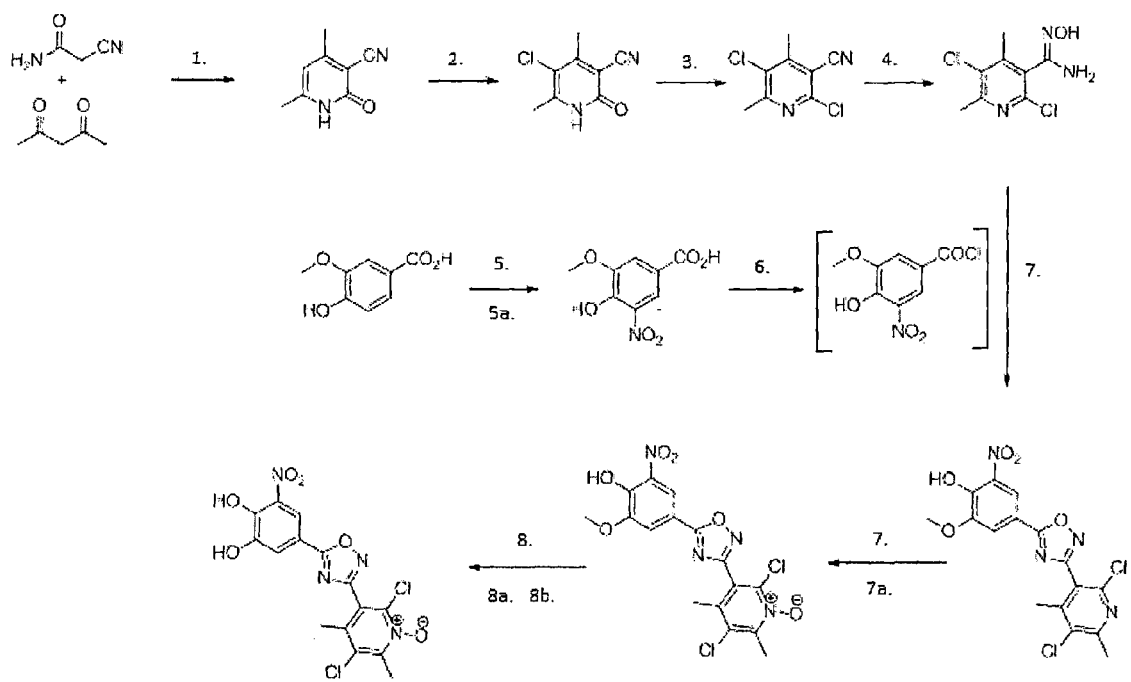

FIG. 3. Process to prepare compound of formula (II) using compound of formula (I) as an intermediate according to one embodiment of the invention.

1. morpholine in MeOH; 2. $SOCl_2$ in acetonitrile; 3. $POCl_3$, $(CH_3)_4NCl$ in DCM; 4. 50% $NH_2OH$ in water, catalytic amount of 1,10-phenantroline hydrate, MeOH; 5. 65% $HNO_3$, acetic acid, 5a. Re-crystallization from acetic acid; 6. $SOCl_2$, DCM, DMF (catalytic), solvent switch from DCM to THF; 6a. addition of acid chloride to amidoxime in DMAc, addition of pyridine, heat to 110° C.; precipitation of DMAc solution aq. HCl with isolation of crude compound of formula (III); crystallization from DCM/EtOH; 7. DCM, UHP, TFAA, solvent switch from DCM to toluene/formic acid; crystallization from toluene/formic acid; 7a. Re-crystallization from formic acid/toluene; 8. AlCl$_3$, NMP, pyridine; the compound of formula (II) is precipitated and isolated by addition of diluted HCl, 8a. reslurry in ethanol 8b. Re-crystallization from IPA/formic acid.

Figure 4:
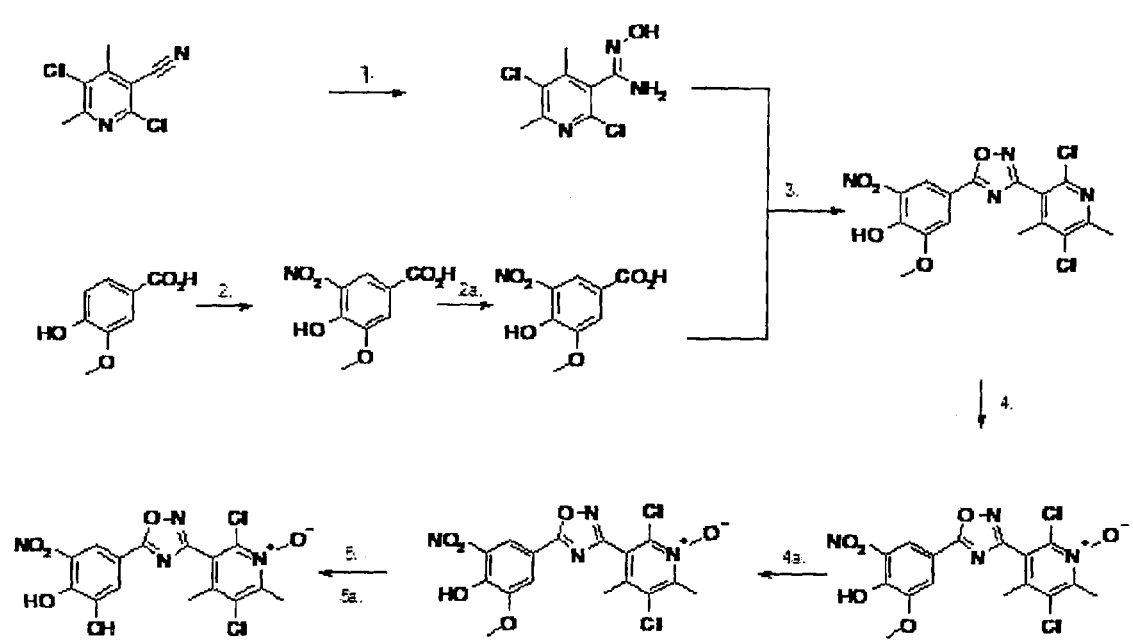

FIG. 4. Process to prepare compound of formula (II) using compound of formula (I) as an intermediate according to one embodiment of the invention.

1. 50% NH$_2$OH in water, catalytic amount of 1,10-phenantroline hydrate MeOH; 2. 65% HNO$_3$, acetic acid, 2a. Re-crystallization from acetic acid; 3. SOCl$_2$, dioxane, addition of acid chloride to amidoxime in dioxane, addition of pyridine, heat to 110° C.; Quench on aq. HCl and DCM; crystallization from DCM/EtOH; 4. DCM, UHP, TFAA, solvent switch from DCM to toluene/formic acid; crystallization from toluene/formic acid; 4a. Re-crystallization from formic acid/toluene; 5. AlCl$_3$, NMP, pyridine; the compound (II) is precipitated and isolated by addition of diluted HCl; 5a. Re-crystallization from IPA/formic acid.

Figure 5:
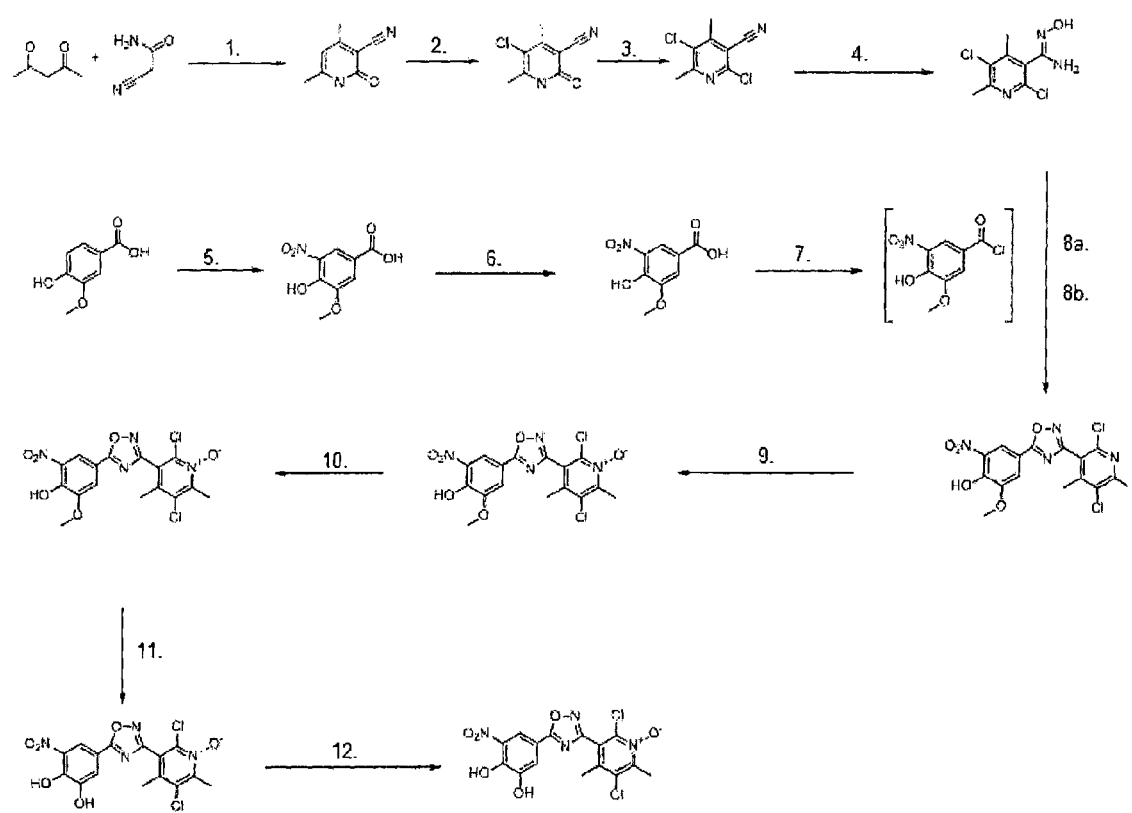

FIG. 5. Process to prepare compound of formula (II) using compound of formula (I) as an intermediate according to one embodiment of the invention.

1. morpholine, MeOH, 2. SOCl$_2$, 3. POCl$_3$; 4. H$_2$NOH, 1,10-phenantroline; 5. HNO$_3$, acetic acid; 6. recrystallization from acetic acid; 7. SOCl$_2$, 1,4-Dioxane; 8a. 1,4-Dioxane, Pyridine; 8b. EtOH; 9. DCM, UHP, TFAA; 10. toluene, formic acid; 11. AlCl$_3$, NMP, Pyridine; 12. Formic acid/IPA.

Figure 6:
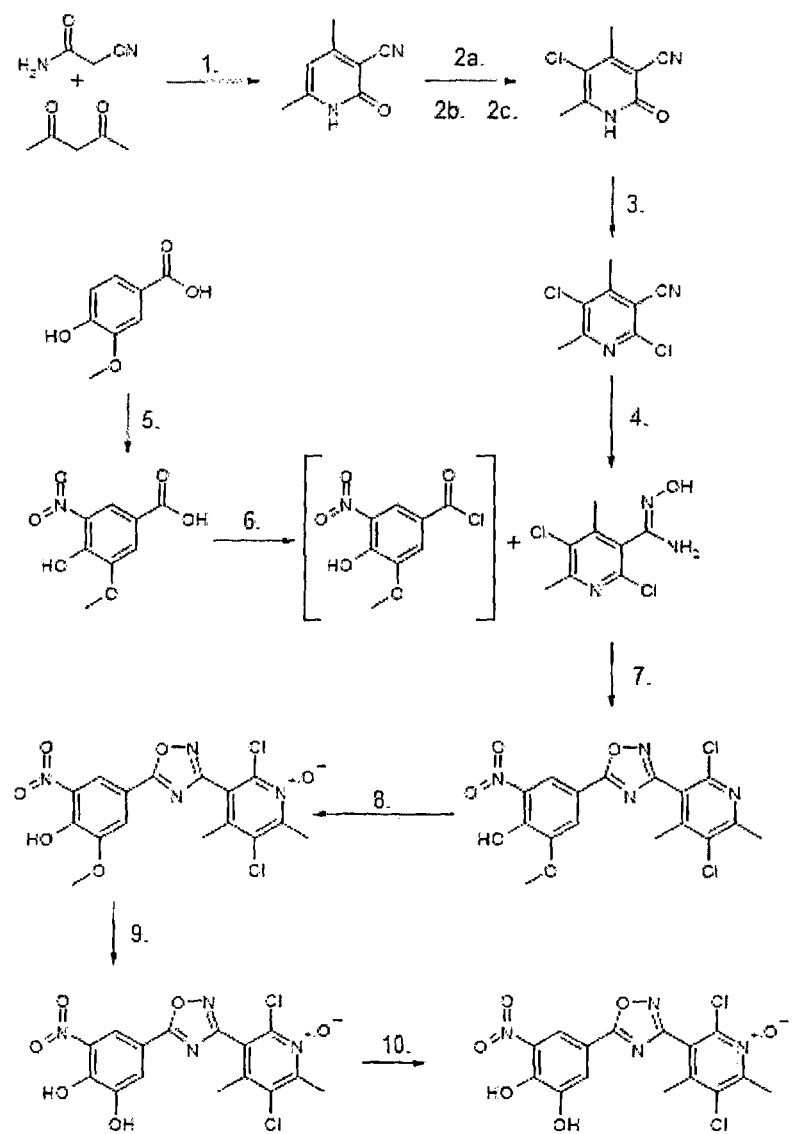

FIG. 6. Process to prepare compound of formula (II) using compound of formula (I) as an intermediate according to one embodiment of the invention.

1. morpholine, MeOH, 22 h, reflux; 2a. SOCl$_2$, MeCN; 2b. 2 h, 65° C.; 2c. 2 h, 20° C.; 3. POCl$_3$, TMACl, 8 h, 110° C.; 4. NH$_2$OH/H$_2$O, 1,10-phenantroline monohydrate, MeOH, 6 h, 75° C.; 5. HNO$_3$, HOAc, 10-20° C.; 6. SOCl$_2$, DCM/DMF, 8 h, 40° C.; 7. DMA/THF, 2 h, 5-10° C.; 8. Urea-H$_2$O$_2$, DCM/TFAA, 18 h, 20° C.; 9. AlCl$_3$, NMP/Pyridine, 2 h, 60° C.; 10. Recrystallization.

DETAILED DESCRIPTION OF THE INVENTION

The present invention provides the compound of the formula (I):

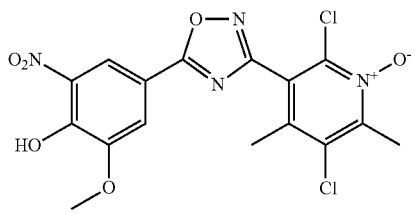

and salts thereof.

The use of the compound of formula (I) leads to a particularly effective process for the preparation of the compound of formula (II). By avoiding the deprotection of both phenolic hydroxyl groups of prior art processes, good yields may be achieved when starting from the readily available and relatively less expensive compound vanillic acid.

The compound of formula (I) may be obtained in high purity, for example in crystalline form, which also helps achieve the preparation of the compound of formula (II) in highly pure forms, for example containing only very low amounts of impurities.

Aptly, the compound of formula (I) is crystallised and/or recrystallized from a mixture of organic solvents one of which is an acid, favourably formic acid. A preferred recrystallization solvent for the compound of formula (I) is a mixture of toluene and formic acid. Another preferred recrystallization solvent system for the compound of formula (I) is formic acid/isopropanol (solvent/antisolvent).

The compound of formula (I) or salt thereof may be prepared by the oxidation of the compound of the formula (III):

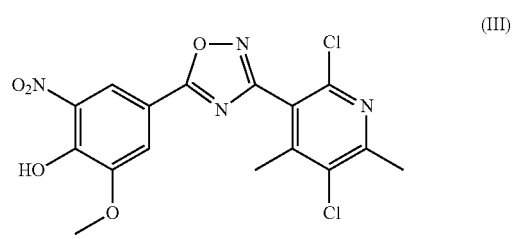 [SMILES: COc1cc(-c2nc(-c3c(Cl)nc(C)c(Cl)c3C)no2)cc([N+](=O)[O-])c1O]

or salt thereof.

Normally and preferably the unsalted compound of formula (I) is prepared from a compound of formula (III) but if a salt is required this may be produced by reaction of the phenolic hydroxyl group with an appropriate base after the formation of the compound of the formula (I).

The oxidation reaction may be performed with any suitable oxidizing agent but preferably a peroxide is employed. Suitably the peroxide may be H$_2$O$_2$ which is preferably employed as H$_2$O$_2$-urea addition complex. The oxidation is preferably carried out in the presence of an organic acid anhydride such as trifluoroacetic anhydride.

The oxidation generally takes place in a non-hydroxylic organic solvent, preferably in halogenated solvents such as methylene chloride. The oxidation is preferably performed at between 15° C. and 30° C., more preferably from 20° C.-25° C.

The compound of formula (III) may be prepared by the reaction of a compound of formula (IV) wherein Y is a halo group, such as chloride, or OR in which R could be hydrogen or a C1-C6 alkyl such as methyl or ethyl:

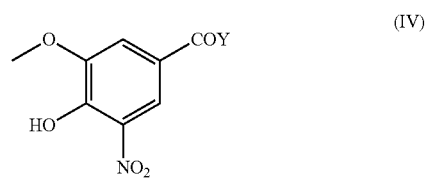

with a compound of the formula (V):

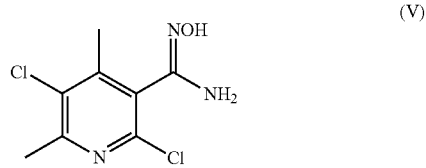

The reaction of the compounds of formula (IV) and (V) can take place in an organic solvent and more generally in a mixture of organic solvents at least one of which will be basic solvent, for example pyridine. A suitable mixed solvent is dimethylacetamide, tetrahydrofuran and pyridine. Alternatively, the solvent organic mixture is a mixture of dioxane and pyridine. The reaction of the compounds of formula (IV) and (V) can also take place in the presence of an organic base such as pyridine or a tertiary amine.

When Y is OR and R is hydrogen in the compound of formula (IV), the compound has formula (IX):

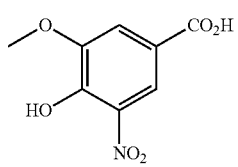

(IX)

When Y is OR and R is hydrogen in the compound of formula (IV), the addition of a coupling reagent such as carbodiimide, phosphonic acid derivatives, carbonyl diimidazole derivatives is required.

When Y is OR and R is C1-C4 alkyl such as methyl, the addition of a Lewis acid such as aluminium trichloride, or a Brönstedt acid such as p-Toluene sulfonic acid catalyst may be required.

When Y is a chloride, compound of formula (VIII), may be preferably used to prepare the compound of formula (III).

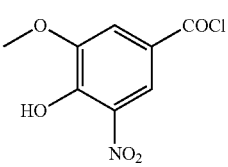

(VIII)

The cyclization process will take place at an elevated temperature, for example at 100° C.-120° C. Particularly the process will be performed at 105° C.-115° C.

If desired a further organic liquid such as ethanol may be added at the end of the reaction. Suitably precipitation is not effected by the addition of such a further organic liquid.

The reaction of the compounds of formulas (IV) and (V) is believed to proceed via the open chain intermediate shown below:

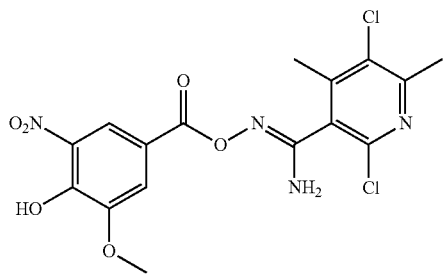 [SMILES: COc1cc(C(=O)O/N=C(\N)c2c(Cl)nc(C)c(Cl)c2C)cc([N+](=O)[O-])c1O]

It is an advantage of the present process that this intermediate need not be isolated but becomes cyclised to the desired compound of formula (III) under the reaction conditions employed. Suitably the reaction is performed at a temperature of between 100-120° C. to give the desired cyclised compound of formula (III).

The use of the compound of formula (VIII) has been found to lead to enhanced yields in comparison with other activated analogues such as those formed from the acid and coupling reagents.

In one embodiment of the present invention the compound of formula (V) is prepared from the compound of the formula (VII)

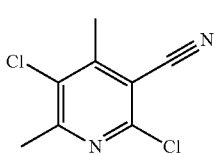

(VII)

by reaction with hydroxylamine in the presence of 1,10-phenanthroline monohydrate. Preferably the reaction is carried in a mixture of methanol and water at 70-80° C. Conveniently, the presence of 1,10-phenanthroline monohydrate reduces or eliminates the formation of unwanted amide and favours the formation of the wanted amidoxime of formula (V).

The compound of formula (IV) may be prepared from the corresponding carboxylic acid by esterification or formation of an acid chloride. Aptly for preparing an acid chloride this may involve reaction with $SOCl_2$. Such corresponding acid may be prepared by nitration of vanillic acid. Compounds of Formula (IV) which are esters may also be prepared by nitration of the corresponding ester of vanillic acid, for example by nitration of the methyl ester of vanillic acid. Suitable conditions for such reactions are set forth in the Examples hereinafter.

The compound of formula (II) in crystalline form is particularly apt for use in pharmaceutical compositions for administration orally. In particular, such compositions may be in the form of discrete unit doses such as tablets or capsules.

The pharmaceutical composition which contains the compound of formula (II) in crystalline form, preferably prepared as described herein, will also comprise a carrier therefor. Suitable carriers include those described in D1, D2 or D3, referred to hereinbefore. The pharmaceutical composition which contains the compound of formula (II) in crystalline form may additionally comprise levodopa (L-DOPA) and/or a peripherally selective aromatic L-amino acid decarboxylase inhibitor (AADCi).

The compound of formula (II) in crystalline form or pharmaceutical compositions thereof may be used to treat some central and peripheral nervous system disorders, such as Parkinson's disease, mood disorders, restless legs syndrome, gastrointestinal disturbances, edema formation states and hypertension. This may be by the administration to a patient in need thereof levodopa, a peripherally selective aromatic amino acid decarboxylase inhibitor and the crystalline compound of formula (II). Such administration is preferably oral administration and employs a discrete unit dose such as a tablet or capsule.

The crystalline compound of formula (II) employed in such compositions is preferably microparticulate, for example as formed by ball milling or by micronization through spiral jet mills. Suitable micronization may be carried out with MCJETMILL® type 200 milling equipment.

Suitably the D10 (EDC (equivalent circle diameter)) is not less than 3, 4, 5 or 6 μm (for example not less than 4 μm), the D50 (EDC) is 5-50, 10-45, 15-30 or 20-25 μm (for example 10-45 μm) and the D95 (EDC) is not more than 60, 70, 80 or 90 μm (for example not more than 90 μm). More suitably the D10 (EDC) is not less than 4 or 5 μm (for example not less than 5 μm), the D50 (EDC) is 10-45 or 15-30 μm (for example 15-30 μm) and the D95 (EDC) is not more than 60 or 70 μm (for example not more than 60 μm).

The following preparations describe an apt process for the preparation of useful intermediates. The following Examples illustrate processes and products according to the invention. These Examples are non-limiting and may be modified in accordance with the description herein and the knowledge of the skilled person.

Preparation of Intermediates
Preparation 1

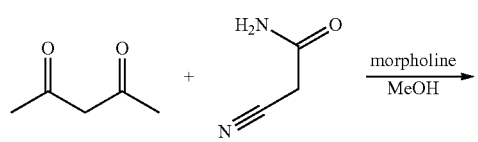

Cyanoacetamide (280 g) was reacted with acetyl acetone (352.9 g) in methanol (1015 g) and morpholine (14.9 g). The reaction was stirred under reflux at 65° C. until the reaction appeared complete. The resulting product suspension was filtered, washed with methanol and dried to provide the desired product about 97% yield.

Preparation 2

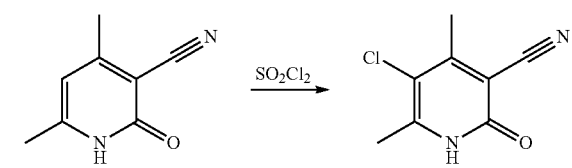

The product of Preparation 1 (159 g) was suspended in acetonitrile (749.5 g) and cooled to 0-5° C. Sulfuryl chloride (178.9 g) was added and the reaction mixture warmed to room temperature and stirred until the reaction appeared complete.

The resulting suspension is cooled to 0-5° C. and filtered. The solid was washed with acetonitrile, ethyl acetate and heptane. The product was then dried under vacuum at 50° C. to yield the desired product (82%).

Preparation 3

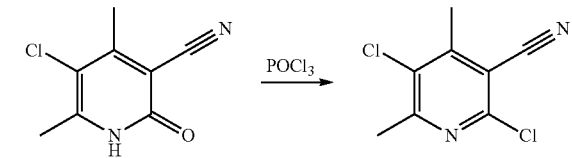

Phosphoryl chloride (973.2 g), tetramethylammonium chloride (67.3 g) and compound of Preparation 2 (227.1 g) were added to dichloromethane (500 g). The suspension was heated to 85° C. and stirred for 5 hours. Excess of phosphoryl chloride was removed by distillation in vacuo. The reaction mixture was cooled below 30° C. and diluted with dichloromethane. The resulting solution was added to water (1350 g) at room temperature and stirred for 30 minutes. The lower organic phase was separate and the aqueous phase extracted with dichloromethane. The organic phases were combined, washed with water and then treated with charcoal. The charcoal was filtered and a solvent swap to heptane was performed by distillation at atmospheric pressure. The solution was filtered at 50° C. and then cooled to 30° C. On further cooling to 0° C. crystals were obtained. These were isolated by filtration, washed twice with heptane. After drying at 50° C. the desired product was obtained typically at 88-91%.

The above process was repeated with a reduction in dichloromethane during crystallisation and adding some methanol. The resulting plate-like crystals were more easily transferred for subsequent use.

Preparation 4a

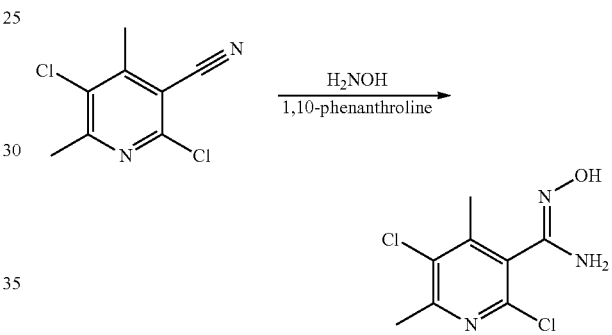

Product of Preparation 3 (68.6 g) and 1,10-phenanthroline monohydrate (0.9 g) were suspended in methanol (240 g) at room temperature. Water (518 g) and a hydroxylamine solution (50% in water, 80.9 g), were added and the mixture heated to 70-80° C. and stirred for 5-6 hours. Water was added at 70-80° C. and the solution held for 1 hour to induce crystallization. Crystallization was completed by cooling to 15° C. over 8 hours. The product was filtered off and washed twice with water and dried at 50° C. under vacuum. The product was an off white to light yellow and the yield was 87.9%.

Preparation 4b

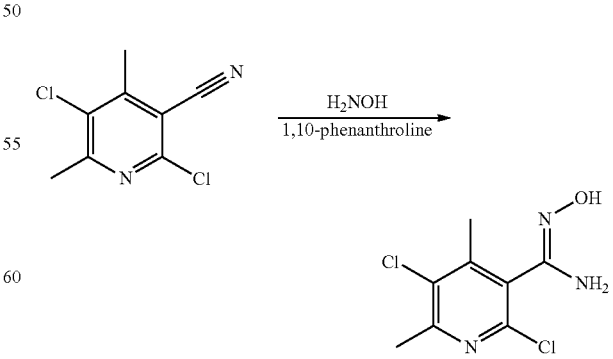

A suspension of 2,5-Dichloro-4,6-dimethyl-nicotinonitrile (45.0 kg) and 50% hydroxylamine (59.2 kg) in the presence of catalytic amount of 1,10-phenanthroline monohydrate (0.680 kg) in methanol/water (214 kg/362 kg) is heated to 70-80° C. The mixture is agitated at 70-80° C. Water (353 kg) is added slowly into the resulting solution while the temperature is maintained at >79° C. The solution is cooled to 75° C. with stirring resulting in crystallization of (Z)-2,5-dichloro-N'-hydroxy-4,6-dimethylnicotinimidamide. The suspension is further cooled to 20° C., the solid is filtered off and the wet cake is washed with water (160 kg). (Z)-2,5-dichloro-N'-hydroxy-4,6-dimethylnicotinimidamide is dried under vacuum at max. 60° C. until residual water level is max 0.15% (KF).

Example 1a

Preparation of 4-hydroxy-5-methoxy-3 nitrobenzoic acid

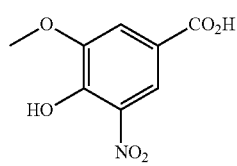

Vanillic acid (75 g) was suspended in acetic acid (788 g). The suspension was cooled to 10° C. to 15° C. and nitric acid (49 g or 65% solution) was added over three hours at a rate which kept temperature between 10° C. and 20° C. The resulting yellow orange was stirred for a further one hour at 18° C. to 23° C. The suspension was filtered off, washed with acetic acid, then a mixture of acetic acid and water (1/2) and then water. Yield of 53% of a 87.9% pure product was obtained.

The above crude product was suspended in acetic acid and warmed to 105° C. to 110° C. until an orange brown solution is obtained. The solution was transferred to the crystallization vessel via a charcoal filter (or polish filtration) at a temperature above 85° C. (optional step). The solution was then cooled to 80° C. to 85° C. The mixture was stirred for one hour at 70° C. to 80° C. (optionally at 75° C.) during which crystallization occurred. The product suspension was cooled to 20° C. to 25° C. for 17 hours or stirred for at least 12 h at 20° C. to 25° C. The product suspension was filtered and washed with acetic acid, then acetic acid/water (1/2) and finally water. The product was dried under vacuum at 50° C. to 55° C. The yield of 70% corresponds to an overall yield of 44% for both parts of this preparation. The purity of the product assayed at 99.7%.

The preceding crystallization step is optional and the solution may be transferred to the crystallization vessel via polish filtration instead of via a charcoal filter.

The post crystallization suspension may be stirred for at least 12 hours at 20° C. to 25° C. as an alternative to 17 hours.

Example 1b

Preparation of 4-hydroxy-5-methoxy-3 nitrobenzoic acid

A reactor was charged with 525 kg of glacial acetic acid and 50 kg vanillic acid. The mixture was heated with warm water gradually to 50° C. in around 75 minutes. Temperature was set to 16° C. Nitric acid, 31.4 kg was then added gradually over a period of 3 hrs. When the administration was complete the mixture was allowed to stir for additional 3.5-4.5 hours. The suspension was centrifuged whilst washed with 25 kg of acetic acid, 50 liter deionised water and 25 kg of acetic acid again. The wet crystalline material was suspended in 165 kg of acetic acid and heated at 91° C. until complete dissolution. The solution was then cooled to 19.8° C. and the mixture was allowed to stir for 1 hr. Centrifugation and washing with 15.2 kg acetic and 40 liter of deionised water was performed. The wet material was then dried in tray vacuum drier between 40-50° C. until constant weight, for 72 hours. The dry material weight was 28.7 kg. The calculated yield was 45.4%.

Example 1c

Preparation of 4-hydroxy-5-methoxy-3 nitrobenzoic acid

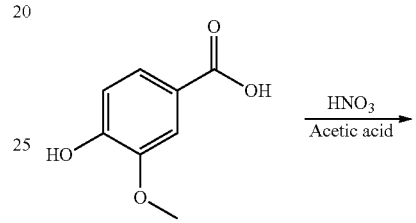

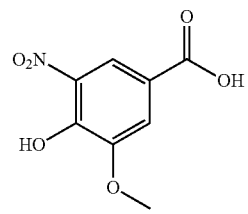

A suspension of vanillic acid (68.8 kg) in acetic acid (720 kg) is cooled to 17° C. before an excess of a 65% nitric acid (44.0 kg) is added. After complete dosage of nitric acid the suspension is stirred for 2 hours. The suspension is filtered off and the wet cake is successively washed with acetic acid (80.0 kg), acetic acid/water (1:2 w/w—105 kg) and finally water (80 kg—if necessary repeat). The solid is dried at 52° C. for NMT 12 hours prior going to next step.

A suspension of the crude solid (650 kg) in acetic acid is warmed to 105° C. and stirred until complete dissolution of the crude solid. After polish filtration, the solution is cooled to 20° C. over 3 h resulting in crystallization and the suspension is stirred for 2 h at 20° C. The solid is filtered off and the wet cake is successively washed with acetic acid (80 kg), acetic acid/water (1:2 w/w—105 kg) and finally water (193 kg—if necessary repeat). 4-hydroxy-5-methoxy-3 nitrobenzoic acid pure is dried under vacuum at max. 55° C. until max 0.5% w/w residual acetic acid and max 0.2% w/w water is reached.

Example 2a

Preparation of 4-hydroxy-5-methoxy-3-nitrobenzoic acid

The process of Example 1a was scaled up to employ vanillic acid (375 g) in acetic acid (3940 g) to which was added nitric acid (65%, 245 g) at 12° C. over 3 hours followed by stirring for one hour. The overall yield was 40% of a 99.9% pure product.

Example 2b

Preparation of 4-hydroxy-5-methoxy-3-nitrobenzoic acid

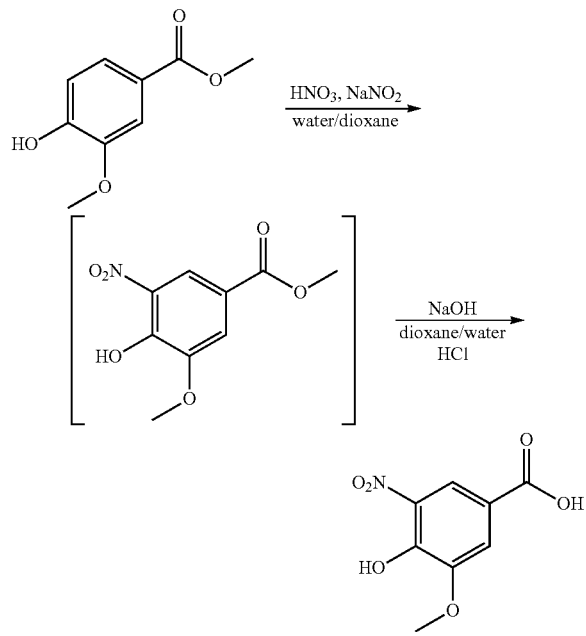

Vanillic acid methyl ester (33 g) and sodium nitrite (0.625 g) are charged. Water (158 mL) and 1,4-dioxane (158 mL) are added at room temperature. The reaction mixture is heated to 40° C. Nitric acid (65%) (15.75 g) is added in the course of three hours and the resulting mixture is stirred for 4 h after addition. The reaction mixture is sampled for completion.

The water/nitric-acid/dioxane azeotrope is distilled off in vacuum at 40° C. The resulting product suspension is quenched by addition of sodium hydroxide solution (50%, 33.2 mL) and then stirred for 16 h. The quench mixture is sampled for completion.

Then, HCl (18.5%, 70.2 mL.) is added until the pH is below 1. The product is filtered off and washed with water (27.9 mL). The product is then dried in vacuum at 50° C. The overall yield was 81% of a 97.3% pure product.

Example 3a

Preparation of 4-hydroxy-5-methoxy-3-nitrobenzoyl chloride

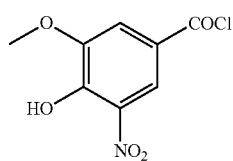

A suspension of compound of Example 1a (1.0 eq) in dioxane (approx 4.5 vol) was treated with thionyl chloride (1.5 eq) and heated to 80° C. A clear solution formed at approximately 75° C. The mixture was stirred for 3 hours at 80° C. Unreacted thionyl chloride was distilled off and after distillation the residue was cooled to 10° C.

Example 3b

Preparation of 4-hydroxy-5-methoxy-3-nitrobenzoyl chloride

A suspension of compound of Example 1a (1.0 eq) in DCM (approx 3.4 vol) is treated with thionyl chloride (1.0-1.2 eq, for example 1.1 eq) and catalytic amount (0.011 eq) of DMF and the mixture is stirred for 16 h at 40° C. DCM is distilled off (approx 2.7 vol) and the residue is diluted with THF (approx 1.8 vol). The excess of thionylchloride is distilled off with THF/DCM and the residue after distillation is cooled to 10° C.

Example 3c

Preparation of 4-hydroxy-5-methoxy-3-nitrobenzoyl chloride

A suspension of compound of Example 1a (1.0 eq) in DCM (approx 4.5 vol) is treated with thionyl chloride (1.0-1.2 eq, for example 1.1 eq) and catalytic amount (0.0055 eq) of DMF and the mixture is stirred for 16 h at reflux. Unreacted thionylchloride is distilled off with DCM and the residue after distillation is diluted with THF (approx 1.8 vol) and cooled to 10° C.

The amount of DCM may be approx 3.4 as an alternative to approx 4.5 vol.

The catalytic amount of DMF may be about 0.011 eq as an alternative to 0.0055 eq.

Example 3d

Preparation of 4-hydroxy-5-methoxy-3-nitrobenzoyl chloride

In a reactor 68 kg dichloromethane, 20 kg 5-nitro-vanillic acid of example 1b, 76 gram of N,N-dimethylformamide and 13.4 kg (8 L) thionyl chloride, was charged at 20.2° C. The mixture was heated to 40° C. until all the starting material dissolved and the evolution of HCl and SO₂ stopped. When all the starting material was consumed 5-10 L dichloromethane was distilled off at normal pressure at 40° C. then the mixture was cooled to 20-25° C. and the distillation was continued until dry under vacuum at 40° C. The evaporation residue was dissolved in 36 kg dry THF. The THF solution was used in Example 4d.

Example 3e

Preparation of 4-hydroxy-5-methoxy-3-nitrobenzoyl chloride

A suspension of product of example 1C (4-hydroxy-5-methoxy-3 nitrobenzoic acid—160 g, 1 eq) in 1,4-dioxane (720 mL, 4.5 vol) is treated with thionyl chloride (169.8 g, 103.7 mL, 1.5 eq) and heated to 80° C. A clear solution is formed at approx. 75° C. The mixture is stirred at 80° C. (3 hours). Unreacted thionyl chloride is distilled off and the residue after distillation is cooled to 10° C.

Example 4a

Preparation of 5-[3-(2,5-dichloro-4,6-dimethyl-pyridin-3-yl)-[1,2,4]oxadiazol-5-yl]-2-hydroxy-3-methoxy-1-nitrobenzene In this example the compound of formula (IV) is reacted with the compound of formula (V) to produce the compound of the formula (III).

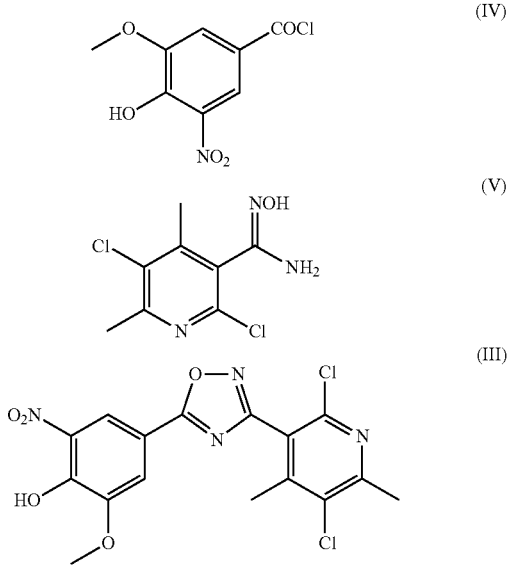

Compound of formula (V) (1.24 eq) was suspended in 1,4-dioxane (approximately 4.5 vol) and the suspension cooled to 10° C. The acyl chloride (compound of formula (IV)) solution of Example 3a in 1,4-dioxane was added slowly maintaining the temperature below 20° C. A clear orange solution was formed. After complete addition, the reaction mixture was stirred at 20° C. for one hour. Pyridine (approximately 8 eq) was added and the reaction mixture heated slowly to 115° C. The mixture was stirred for 6 hours at 115° C. and then cooled to 20° C.

The dioxane/pyridine was distilled off under vacuum at 70° C. The residue was kept at 80° C. and ethanol (approx 8 vol) added to induce crystallization. The resulting yellow suspension was cooled to 0° C. and stirred for two hours. The product was filtered off and washed with ethanol (2.5 vol) water (3.8 vol) and ethanol 2.5 vol). The product was dried under vacuum at 50° C. Typical yields for this process are 82 to 85%.

In an optional variant, methanol was employed in place of ethanol to induce crystallization.

Example 4b

Preparation of 5-[3-(2,5-dichloro-4,6-dimethyl-pyridin-3-yl)-[1,2,4]oxadiazol-5-yl]-2-hydroxy-3-methoxy-1-nitrobenzene In a different reactor, compound of formula (V) (1.1 eq) is dissolved in DMAc (approx 5.8 vol) and the solution is cooled to 5° C. The benzoyl chloride solution of Example 3b in THF/DCM is then added slowly maintaining the temperature below 10° C. After complete addition, the reaction mixture is stirred at 20±5° C. Pyridine (1.3 to 1.6 eq, for example 1.5 eq) is charged and the reaction mixture is heated slowly to 110±5° C. removing low boiling components by distillation. The mixture is stirred for additional 3 h at 110±5° C.

In a further reactor, concentrated HCl (23.8 eq) is diluted with water (approx. 8.5 vol) and cooled to 10° C. The reaction mixture in pyridine is dosed slowly to diluted hydrochloric acid. After complete addition, the resulting suspension is stirred for additional 2 h and the solid is filtered off. The crude solid is washed once with water and pre-dried on funnel.

The crude solid is suspended in DCM (approx. 28.6 vol) and the suspension is heated to 40° C. to reach a clear solution. Resulting solution is cooled to 20° C. and extracted with water. After phase separation, the aqueous phase is re-extracted with DCM and combined organic phase are washed once with water. DCM is distilled off under vacuum followed by addition of ethanol. Resulting suspension is further distilled to reduce the amount of DCM, then cooled to 5° C. and stirred for additional 2 h. Finally, the product is filtered off, washed once with cold ethanol and dried under vacuum at 45° C.

Example 4c

Preparation of 5-[3-(2,5-dichloro-4,6-dimethyl-pyridin-3-yl)-[1,2,4]oxadiazol-5-yl]-2-hydroxy-3-methoxy-1-nitrobenzene In a second reactor, compound of formula (V) (1.1 eq) is dissolved in DMAc (approx. 7 vol) and the solution is cooled to 5° C. The benzoyl chloride solution of Example 3c in THF/DCM is added slowly maintaining the temperature below 10° C. After complete addition, the reaction mixture is stirred at 20±5° C. for 30 min Pyridine (6.9 to 7.3 eq, for example 7.14 eq) is charged and the reaction mixture is heated slowly to 110° C. removing low boiling components by distillation. The mixture is stirred for additional 4 h at 110° C. and cooled to 20° C.

In a third reactor an emulsion of diluted hydrochloric acid (prepared from conc. HCl (19.6 eq) and approx. 7.6 vol distilled water) and DCM (approx. 25.5 vol) is cooled to about 15° C. before the reaction mixture in pyridine is dosed slowly to the emulsion. After complete addition, the organic phase is separated and washed with water before DCM is distilled off under vacuum followed by addition of ethanol. The resulting suspension is further distilled to reduce the amount of DCM, then cooled to 5° C. and stirred for additional 2 h.

Finally, the product is filtered off, washed once with cold ethanol and dried under vacuum at 45° C.

Example 4d

Preparation of 5-[3-(2,5-dichloro-4,6-dimethyl-pyridin-3-yl)-[1,2,4]oxadiazol-5-yl]-2-hydroxy-3-methoxy-1-nitrobenzene 140 kg N,N-dimethyl acetamide was charged into the reactor. 24.2 kg of amidoxime of Preparation 4 was dissolved in N,N-dimethyl acetamide while stirring at 21° C. The solution was cooled to 5-10° C. The THF solution of Example 3d was introduced slowly into the reaction mixture, 1.5-2 hrs, while the internal temperature was maintained at max. 9.5° C. by external cooling. When the addition was complete the external cooling was stopped. The internal temperature was allowed to raise to 21° C. in an hour. After stirring for 30 minutes, pyridine 53.0 kg was added to the mixture, while the temperature was in the range of 22.4° C.-20.6° C. Heating was started and the internal temperature raised to 105-115° C. The mixture started to reflux for 3 h while the internal temperature managed to 113° C. by partial distillation of some THF. The reaction mixture was then cooled and introduced to a mixture of 220 kg concentrated HCl and 170 kg of deionised water while the internal temperature was maintained between 14-16° C. The reactor was rinsed with 10 kg of N,N-dimethylacetamide and 20 kg deionised water. The rinse liquid was run to the mixture. The suspension was then further cooled to 5-10° C. and stirred for 1.5-2.0 hours. The product was centrifuged and was washed 80 kg deionised water. Crude wet weight of the product was 88.6 kg.

The crude wet product, was dissolved in 460 kg (340 L) dichloromethane at max 40° C. When dissolved the temperature was set to 20-30° C. and 120 kg deionised water was added. The organic phase was separated, the inorganic phase was extracted with 80 kg dichloromethane. The organic phase of 460 kg, was then washed with 200 kg deionised water and the phases were separated. The inorganic phase was extracted with the 80 kg dichloromethane and the organic phases were unified. The organic phase obtained so was concentrated in vacuum at 35° C. to 200-240 Liter, then 260 kg ethanol 96% was continuously added and the evaporation was continued to a final 200-240 liter volume. Then the mixture was cooled to 5-10° C. and was allowed to stir for 3 hrs. Centrifuging, washing with 20 kg ethanol resulted in 35.4 kg wet product. Vacuum drying for 16 hours at 45° C. gave 34.09 kg dry product. The yield was 79.9%.

Example 4e

Preparation of 5-[3-(2,5-dichloro-4,6-dimethyl-pyridin-3-yl)-[1,2,4]oxadiazol-5-yl]-2-hydroxy-3-methoxy-1-nitrobenzene In a second vessel, (Z)-2,5-dichloro-N'-hydroxy-4,6-dimethylnicotinimidamide (201.2 g, 1.24 eq) is suspended in 1,4-dioxane (720 mL, 4.5 vol) and the suspension is cooled to 10° C. The residue of example 3e in 1,4-dioxane is added slowly maintaining the temperature below 20° C. A clear orange solution is formed. After complete addition, the reaction mixture is stirred at 20° C. for 1 hour. Pyridine (483.7 mL, 8 eq) is then charged and the reaction mixture is heated slowly to 115° C. The mixture is stirred at 115° C. for 6 hours. The solution is then cooled to 20° C. Dioxane/pyridine is distilled off.

After distillation, the pit is kept at 80° C. and ethanol (1.28 L, 8 vol) is added at this temperature to induce crystallization. The resulting yellow suspension is cooled to 75° C. and stirred for 1 h at this temperature to allow crystal growth. The product suspension is then cooled to 0° C. and stirred for 2 h at this temperature. The product is filtered off and washed subsequently with ethanol (400 mL, 2.5 vol), water (608 mL, 3.8 vol) and ethanol (400 mL, 2.5 vol). The product is dried under vacuum at 50° C. until LOD is max 1% w/w.

Example 4f

Preparation of 5-[3-(2,5-dichloro-4,6-dimethyl-pyridin-3-yl)-[1,2,4]oxadiazol-5-yl]-2-hydroxy-3-methoxy-1-nitrobenzene A mixture of compound of formula (V) (11.7 g, 50 mmol, 1.25 eq), methyl 4-hydroxy-3-methoxy-5-nitrobenzoate (10 g, 40 mmol, 1 eq) and a catalytic amount of p-toluenesulfonic acid (0.76 g, 4 mmol, 1 eq) in dimethyl acetamide was heated to 80° C. The reaction was followed by HPLC. After 23 h, 6% of conversion was obtained.

Example 4g

Preparation of 5-[3-(2,5-dichloro-4,6-dimethyl-pyridin-3-yl)-[1,2,4]oxadiazol-5-yl]-2-hydroxy-3-methoxy-1-nitrobenzene A mixture of compound of formula (V) (11.7 g, 50 mmol, 1.25 eq), methyl 4-hydroxy-3-methoxy-5-nitrobenzoate (10 g, 40 mmol, 1 eq) and a catalytic amount of aluminum chloride (0.53 g, 4 mmol, 0.1 eq) in dimethyl acetamide was heated to 80° C. The reaction was followed by HPLC. After 20 h, 10% of conversion was obtained.

Example 5a

Preparation of 5-[3-(2,5-dichloro-4,6-dimethyl-1-oxy-pyridin-3-yl)-[1,2,4]oxadiazol-5-yl]-2-hydroxy-3-methoxy-1-nitrobenzene

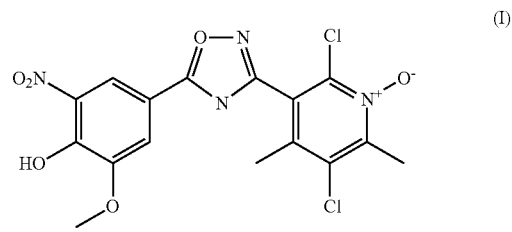

(I)

A solution of the product of Example 4a (24 g) was dissolved in dichloromethane (388 g) at 20-40° C. The yellow solution was cooled to 5° C. and urea hydrogen-peroxide (UHP) (17.6 g) and trifluoroacetic acid anhydride (37 g) added and stirring continued for 12 hr at 5° C. The reaction mixture was warmed to room temperature over one hour and stirring continued for a further five hours. The precipitate that formed was filtered off and washed with dichloromethane. The combined filtrates were diluted further with dichloromethane, all washed and concentrated at atmospheric pressure. Toluene was added and the resulting suspension concentrated under vacuum, to remove residual dichloromethane. Further toluene was added and the mixture checked to ensure less than 0.5% dichloromethane and less than 0.1% water was present. Formic acid was added to provide a 10-12% formic acid in toluene mixture. The resulting suspension was warmed to 90° C. and stirred until complete dissolution of solid. Crude product was obtained by cooling the solution to 5-10° C. until crystallization commenced. The suspension was agitated at 5-10° C. until crystallization appeared complete. The solid was filtered off, washed with toluene and dried under a stream of nitrogen.

The crude product was suspended in 10-12% wt/wt solution of formic acid in toluene and warmed to 90° C. until dissolution of the solid. The solution was cooled to 5° C. and stirred at 5° C. until crystallisation occurred. The solid was obtained by filtration and washed with toluene. This recrystallization was repeated until the product tested as containing less than 0.1% of starting material. The pure product was dried under vacuum at 50° C.

Example 5b

Preparation of 5-[3-(2,5-dichloro-4,6-dimethyl-1-oxy-pyridin-3-yl)-[1,2,4]oxadiazol-5-yl]-2-hydroxy-3-methoxy-1-nitrobenzene After dissolution of the product of Example 4b (24 g) in DCM (388 g) at 20-40° C. the yellow solution is cooled to 5° C. before the temperature controlled addition of urea hydrogen peroxide complex (UHP)(17.6) and trifluoroacetic anhydride (TFAA) (37 g). After addition of TFAA is complete stirring is continued for 12 h at 5° C. before the reaction mixture is warmed to room temperature (RT) within 1 h and stirring is continued for additional 5 h. The precipitate formed during the reaction is filtered and washed with DCM on the funnel filter. The combined filtrates are diluted with DCM (325 g) and then repeatedly washed with water before concentrated at atmospheric pressure. DCM is replaced by toluene (170 g) and the resulting suspension is concentrated again under vacuum to remove surplus DCM. Distillates are replaced by fresh toluene as before and the mixture is analyzed for residual water and DCM (Residual DCM after solvent switch max. 0.5%; residual water after solvent switch max. 0.1%). Formic acid (24 g) is charged resulting in an approx. 10-12% w/w formic acid in toluene solvent mixture The resulting suspension is warmed to 90° C. and stirred until compete dissolution of the solid is achieved. The crude product is crystallized by cooling of this solution to 5-10° C. and subsequent agitation of the resulting suspension at 5-10° C. The solid is filtered of washed with toluene and then dried in a stream of nitrogen gas.

The crude product so obtained is suspended in an approx. 10-12% w/w solution (176 g) of formic acid in toluene. The suspension is warmed to 90° C. and stirred until all product is dissolved. After cooling of this solution to 5° C. and subsequent stirring at 5° C., crude product is isolated by filtration and subsequent washing of the wet product with toluene.

The re-crystallization of crude product is repeated (2 or more times). The pure product (11.8 g) is dried at 50° C. under vacuum.

Example 5c

Preparation of 5-[3-(2,5-dichloro-4,6-dimethyl-1-oxy-pyridin-3-yl)-[1,2,4]oxadiazol-5-yl]-2-hydroxy-3-methoxy-1-nitrobenzene After dissolution of the product of Example 4c (24 g) in DCM (388 g) at 20-40° C. the yellow solution is cooled to 5° C. prior to the temperature controlled addition of urea hydrogen peroxide complex (UHP) (17.6 g) and trifluoroacetic acid anhydride (TFAA) (37 g). After addition of TFAA is complete stirring is continued for 12 h at 5° C. before the reaction mixture is warmed to RT within 1 h and stirring is continued for additional 5 h. The precipitate formed during the reaction is filtered and the filter cake is washed with DCM. The combined filtrates are diluted with DCM (325 g) and then repeatedly washed with water before concentrated at atmospheric pressure. DCM is replaced by toluene (170 g) and the resulting suspension is concentrated again in vacuum in order to remove surplus DCM and water. Distillates are replaced by fresh toluene followed by addition of formic acid (24 g). The resulting suspension is warmed to 80° C. and stirring is continued in order to dissolve the solid. The product is crystallized by cooling of this solution to 5° C. and subsequent agitation of the resulting suspension at 5° C. The solid is filtered, washed with toluene and then dried in a stream of nitrogen gas.

The product is suspended in a formic acid/toluene (18 g/158 g) mixture followed by warming of the reaction mixture to 80° C. After dissolution of the product the solution is cooled to 5° C. whereby the product precipitates. After additional stirring at 5° C. the suspension is filtered and the filter cake is washed with toluene.

The re-crystallization of the product is repeated. The product is used as a wet material in the next process step (12.1 g product obtained if dried at max. 60° C.).

Example 5d

Preparation of 5-[3-(2,5-dichloro-4,6-dimethyl-1-oxy-pyridin-3-yl)-[1,2,4]oxadiazol-5-yl]-2-hydroxy-3-methoxy-1-nitrobenzene 550 kg (420 L) Dichloromethane was charged into a reactor. 34 kg of product of example 4d was added to in a short period at 20° C. internal temperature. The solution was cooled to 6.5° C. then 24.9 kg urea hydrogen peroxide complex (UHP) was added over a period of 20-40 minutes between 5-10° C. Stirring was continued for additional 20 minutes between 6.5-7.5° C. Trifluoroacetic anhydride, 53 kg, was administered into the reaction mixture, starting and maintaining the temperature at 6-7° C. over a period of 2-3 hours. When the administration was complete the mixture was stirred for additional 30 minutes. Then the internal temperature was allowed to rise to a maximum of 25° C. over a period of 1.5 hours. The internal temperature was maintained between 20-25° C. and the mixture was allowed to react for additional 18-20 hrs. The reaction mixture was centrifuged and the fuge was washed with 45 kg dichloromethane. To the separated dichloromethane solution 460 kg (350 L) dichloromethane and 190 kg deionised water was added. The mixture was stirred for 10 minutes and the phases were separated for 30 minutes. The organic phase was washed again with 2×190 kg deionised water and separated as previously. Evaporation of the unified organic solution at max 35° C. under vacuum was done to a final volume of 100-120 L. Then a total of 105 kg acetonitrile was administered into the system while the distillation was continued to keep the volume at 100-120 L. When complete an additional 170 kg (220 L) acetonitrile was added to the mixture at normal pressure. This suspension was heated to 70-80° C. at normal pressure while dichloromethane was distilled off continuously. The mixture was then kept stirred for an hour. The suspension was cooled to 20-25° C. and was stirred for an additional 30 minutes. The suspension was then centrifuged and was washed with 30 kg acetonitrile. The wet material, 29.7 kg, was vacuum dried for 16 hrs at 30° C. Dried product yield was 81.5%.

27.7 kg product, 240 kg toluene and 29.2 kg formic acid was charged into reactor then heated to 90° C. for complete dissolution for 1 hour. Then the solution was cooled to 7° C. and then the suspension was kept at 7° C. for additional 2 hrs. If necessary seeding was applied with 3-5 grams of pure product. The suspension was then centrifuged for 1 hour whilst washing with 28 kg cold toluene. The product was suspended in 225 kg toluene and 27.2 kg formic acid was charged. The mixture then was heated to 90° C. for complete dissolution for 1 hour. Then the solution was cooled to 20-25° C., then the suspension was kept between 15-25° C. for additional 2 hrs, seeded if necessary. The suspension then was centrifuged for 60 minutes whilst washed with 28 kg cold toluene. The recrystallization process may be repeated 2-3 more times.

Drying for 24 hrs at 38-41° C. under vacuum was conducted until constant weight. This resulted in 16.34 kg (58.8%) dry material.

Example 5e

Preparation of 5-[3-(2,5-dichloro-4,6-dimethyl-1-oxy-pyridin-3-yl)-[1,2,4]oxadiazol-5-yl]-2-hydroxy-3-methoxy-1-nitrobenzene After dissolution of the product of Example 4e (150 g) in DCM (2.43 kg) at reflux, the yellow solution is cooled to 5° C. prior to the temperature controlled addition of carbamide peroxide (UHP—urea hydrogen peroxide) (110 g) and trifluoroacetic acid anhydride (TFAA) (155.1 ml in 4 portions within 2 hours). The mixture is stirred for 12 h at 5° C. then the reaction mixture is warmed to 25° C. over 1.5 hours and stirred for 5 hours. The precipitate formed during the reaction is filtered and the filter cake is washed with DCM (0.36 kg). The combined filtrates are warmed to 30° C. and diluted with water (300 g). 10% sodium hydroxide is added until pH=4 is reached. The biphasic system is stirred for 10 minutes at 30° C. and the mixture is then allowed to separate. The organic layer is then successively washed with a mixture water (750 g) and 10% sodium hydroxide (7.5 g) (until pH=4), 3.2% HCl solution (300 g). DCM is distilled at atmospheric pressure and then replaced by toluene (1035 g) applying vacuum (150 mbar) and keeping internal temperature at 45° C. Formic acid (300 g) and toluene (900 g) are added keeping the internal temperature above 40° C. The resulting solution is distilled under vacuum (150 mbar, 45° C. internal temperature) until distillation ceases. After seeding at 45° C., the slurry is stirred for 1 hour at 45° C. then is cooled to 5° C. over 2 hours. The suspension is stirred for at least 2 hours at 5° C. and then filtered. The wet cake is washed with toluene (195 g) and dried in a stream of nitrogen gas (Chemical purity of crude product min. 92% area).

A suspension of crude product in formic acid (388 g, 2 wt) is warmed to 55° C. and stirred until complete dissolution of the crude product. Toluene (1242 g, 6.4 wt) is added maintaining the internal temperature above 50° C. The reaction is stirred at 150 mBar and internal temperature 45° C. until distillation ceases. The vacuum and distillation is stopped and then seed is added at 45° C. The slurry is stirred for 1 hour at 45° C. and cooled to 5° C. in 2 hours. The resulting suspension is stirred for at least 2 hours at 5° C. then filtered. The wet cake is washed with toluene (260 g, 1.34 wt). The wet cake is collected and charged into the reactor. This procedure is repeated at least twice until 5-[3-(2,5-dichloro-4,6-dimethyl-pyridin-3-yl)-[1,2,4]oxadiazol-5-yl]-2-hydroxy-3-methoxy-1-nitrobenzene level max is 0.1% (a/a) prior to dry at 25° C. max under vacuum.

Example 6

Example 5a was repeated on a larger scale employing product of Example 3 (82 g), dichloromethane (1325 g), urea peroxide (60.1 g) and trifuoroacetic acid anhydride (128 g).

Example 7a

Preparation of 5-[3-(2,5-dichloro-4,6-dimethyl-1-oxy-pyridin-3-yl)-[1,2,4]oxadiazol-5-yl]-3-nitrobenzene-1,2-diol

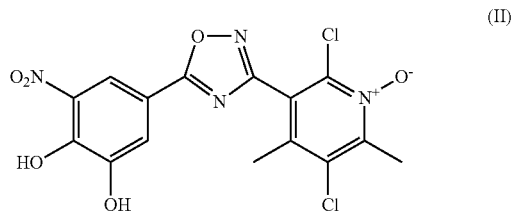 [SMILES: Cc1c(Cl)c(C)[n+]([O-])c(Cl)c1-c1noc(-c2cc(O)c(O)c([N+](=O)[O-])c2)n1]

(II)

Product of Example 6 (15 g) was suspended in N-methyl pyrrolidone (NMP) (131.5 g) and cooled to 5° C. Aluminium chloride (6.2 g) and pyridine (12 g) were added while maintaining the temperature at 5° C. After the addition of pyridine was complete the reaction mixture was warmed to 60° C. and maintained for 2 hours. After confirmation that less than 0.5 starting material remained, the reaction mixture was cooled, and aqueous HCl (water 233 g, HCl 123 g, 37%) added. The resulting yellow solid was isolated by suction filtration. The resulting wet product was washed with water and propan-2-ol (67 g) and dried under vacuum.

Optionally, the crude product was suspended in ethanol (492 g) and warmed to reflux. The suspension was stirred for 1 hour under reflux and then cooled to room temperature. The solid was obtained by filtration, washed with ethanol and dried under vacuum at 50° C. A typical yield of 85% was achieved.

If desired either the final ethanol crystallised material or the initially produced product after washing with propan-2-ol may be employed in preparation of micronized material for use in pharmaceutical compositions.

Example 7b

Preparation of 5-[3-(2,5-dichloro-4,6-dimethyl-1-oxy-pyridin-3-yl)-[1,2,4]oxadiazol-5-yl]-3-nitrobenzene-1,2-diol An approx. 11% w/w suspension of the product of example 5b (20 g) in NMP (150 g) is cooled to 5° C. followed by a consecutive temperature controlled addition of aluminium chloride (8 g) and pyridine (15.3 g). After addition of pyridine is complete the reaction mixture is warmed to 60° C. followed by additional 2 h reaction time. After complete conversion of the product of example 5b the reaction mixture is cooled before an aqueous diluted hydrochloric acid (water 293 g, HCl 177 g, 34%) is dosed. By addition of the hydrochloric acid, crude product precipitates from the NMP/water matrix as a yellow solid which is isolated by suction filtration. The resulting wet product is washed with water and 2-propanol in a replacement wash followed by drying of the wet crude product under vacuum.

The crude product is suspended in ethanol (282 g) followed by warming of the mixture to reflux. The suspension is stirred for 1 h at reflux conditions followed by cooling to room temperature. The product is isolated by filtration of the suspension. The wet product is washed with ethanol and subsequently dried in vacuo at approx 50° C. (typically weight corrected yield was 85%).

The product (20 g) is suspended in formic acid (725 g) before the resulting suspension is warmed to max. 67° C. Stirring is continued until complete dissolution of the product is achieved. The hot solution is filtered and the filtrate is cooled to 40-45° C. before the product is precipitated first by concentration of the solution to approx. 40% (v/v) of its original volume followed by addition of the anti solvent 2-propanol (390 g). After addition of 2-propanol is finished the resulting suspension is kept at 55-60° C. for crystal ripening followed by cooling to RT and filtration. The filter cake is washed with 2-propanol followed by drying of the material at max. 58° C. until loss on drying (LOD) max. 0.5%. Typically, a yield of 97-98% was obtained.

If desired the product may be employed in preparation of micronized material for use in pharmaceutical compositions.

Example 7c

Preparation of 5-[3-(2,5-dichloro-4,6-dimethyl-1-oxy-pyridin-3-yl)-[1,2,4]oxadiazol-5-yl]-3-nitrobenzene-1,2-diol A suspension of the product of example 5c (20 g) or of example 6 (20 g) in NMP (153 g) is cooled to 5° C. followed by a consecutive temperature controlled addition of aluminium chloride (8.2 g) and pyridine (15.4 g). After addition of pyridine is complete the reaction mixture is warmed to 60° C. followed by additional 3 h reaction time. After complete conversion of the product of example 5c or of example 6 the crude product is precipitated by a temperature controlled addition of an aqueous hydrochloric acid solution (water 296 g, HCl 179 g, 34%). Filtration of the solid followed by washing of the wet filter cake with water and 2-propanol yields a crude product wet material which is immediately dissolved in formic acid (536 g). After polish filtration the filtrate is concentrated under vacuum followed by addition of the anti-solvent 2-propanol (318 g). After aging of the resulting suspension at 55-60° C. the suspension is cooled to RT and filtered. The wet filter cake is washed with 2-propanol. The wet product is dried under vacuum at max. 58° C. until LOD max. 0.5%. The yield was in the range of 70-95%

If desired the product may be employed in preparation of micronized material for use in pharmaceutical compositions.

Example 7d

Preparation of 5-[3-(2,5-dichloro-4,6-dimethyl-1-oxy-pyridin-3-yl)-[1,2,4]oxadiazol-5-yl]-3-nitrobenzene-1,2-diol 132 kg (147 L) N-methylpyrrolidone was charged into a 1000 L reactor. 16.3 kg of product of example 5d was then added. The suspension was cooled to 5-7° C. and 6.5 kg of sublimed aluminium chloride was added in portions keeping the internal temperature between 5-10° C. The mixture was stirred for 10 minutes then 12.6 kg pyridine was added maintaining the internal temperature between 5-10° C. The mixture was warmed with water in the jacket to 20-25° C. and the mixture was stirred for 30 minutes. Then the mixture is heated to 58-62° C. and reacted for around 2 hours. In a separate reactor a mixture of 240.5 kg deionised water and 146.4 kg concentrated HCl was mixed. This was cooled to 15-20° C. The reaction mixture from the demethylation was introduced into the diluted hydrochloric acid between 20-25° C. Optionally, 51.2 kg dichloromethane was added to the suspension, stirred for 30 minutes and was centrifuged, washed with 60 kg deionised water and 20 kg isopropanol. Drying gave 15.9 kg of product.

The product was suspended in 185.3 kg of ethanol. The mixture was then stirred at 78° C. for an hour, then cooled to 20-25° C. and stirred for 1 hour. The suspension was then centrifuged and the filtercake was washed with 44.5 kg ethanol, 96%. The solid material was dried at 50° C. in vacuum in a stainless steel tray drier. 14.35 kg (90.3% yield) dry product was obtained.

A reactor was charged with 317.2 kg formic acid and dry product. The mixture was heated to 65° C. until all the solid dissolves. The hot solution was then filtered to an empty 1000 L reactor, was rinsed with 20 kg formic acid, then the formic acid solution was distilled partially off under vacuum to around 80-100 L. 260 kg isopropanol was then introduced at 50-60° C. and stirred for 30-35 minutes. The mixture was then cooled to 20-25° C. with water in the jacket and was allowed to stir min 2 hours. The suspension was then centrifuged and was washed with 25 kg isopropanol. The wet material was removed from the fuge and was transferred into vacuum tray drier and was dried until constant weight under vacuum at 45-50° C. resulting in 13.6 kg product, with a yield of 95.3%.

If desired the product may be employed in preparation of micronized material for use in pharmaceutical compositions.

Example 7e

Preparation of 5-[3-(2,5-dichloro-4,6-dimethyl-1-oxy-pyridin-3-yl)-[1,2,4]oxadiazol-5-yl]-3-nitrobenzene-1,2-diol A suspension of product of Example 5e (34.1 kg) in N-Methyl pyrrolidone (NMP) (182 kg) is warmed to 50° C. until dissolution and then cooled to 5° C. followed by a consecutive temperature controlled addition of aluminium chloride (9.8 kg) and pyridine (18.2 kg). After addition of pyridine is complete the reaction mixture is warmed to 60° C. and stirred for at least 2 hours. The reaction mixture is cooled to 10-16° C. (e.g. 11, 13, 15° C.) before an aqueous diluted hydrochloric acid (4M solution, 283 L) is dosed maintaining the temperature below 25° C. During the addition of the hydrochloric acid the crude product is precipitated from the NMP/water matrix as a yellow solid. The yellow solid is filtered and subsequently washed with water (179 kg), 2-propanol (105 kg). The wet solid is dried under vacuum at 55° C.

A suspension of wet product (25.1 kg) in formic acid (813 kg) is warmed to max. 67° C. The mixture is stirred at 67° C. until complete dissolution of the product is achieved. The hot solution is filtered and the filtrate is cooled to 40-45° C. before the product is precipitated first by concentration of the solution to approx. 40% (v/v) of its original volume followed by addition of the anti solvent 2-propanol (380 kg). After addition of 2-propanol the resulting suspension is stirred at 55-60° C. for crystal ripening followed by cooling to RT and filtration. The filter cake is washed with 2-propanol (38 kg) and then dried at max. 58° C. until LOD max. 0.5%). The product may be milled (for example using the method of Example 8).

Example 8

Micronization of 5-[3-(2,5-dichloro-4,6-dimethyl-1-oxy-pyridin-3-yl)-[1,2,4]oxadiazol-5-yl]-3-nitrobenzene-1,2-diol with MC JETMILL® type 200 milling equipment (micronization through spiral jet mills)

Equipment:
Mill: MC JETMILL® 200
Dosing unit: K-Tron T 35
Cyclone: type 600

Each micronization trial was performed on at least 2 kg of 5-(3-(2,5-dichloro-4,6-dimethyl-1-oxy-pyridin-3-yl)-[1,2,4]oxadiazol-5-yl]-3-nitrobenzene-1,2-diol.

The following working parameters have been defined for the micronization:
Feed rate range: 24.0-48.0 kg/h (200-400 g/30 sec.)
Mill pressure range: 3.0-4.0 bar
Venturi pressure range: 3.0-4.0 bar; preferably the Venturi pressure is the same as the mill pressure Using the above equipment and working parameters the microparticles of 5-[3-(2,5-dichloro-4,6-dimethyl-1-oxy-pyridin-3-yl)-[1,2,4]oxadiazol-5-yl]-3-nitrobenzene-1,2-diol comply with the following particle size specification (particle size determined by optical microscopy): D10 (EDC) is not less than 4 or 5 μm (for example not less than 5 μm), the D50 (EDC) is 10-45 or 15-30 μm (for example 15-30 μm) and the D95 (EDC) is not more than 60 or 70 μm (for example not more than 60 μm).

Example 9 (FIG. 5)

2,5-Dichloro-4,6-dimethyl-nicotinonitrile is reacted with hydroxylamine in the presence of catalytic amounts of 1,10-phenanthroline monohydrate to yield the aldoxime (Z)-2,5-dichloro-N'-hydroxy-4,6-dimethylnicotinimidamide which represents the first coupling partner towards the synthesis of 5-[3-(2,5-dichloro-4,6-dimethyl-pyridin-3-yl)-[1,2,4]oxadiazol-5-yl]-2-hydroxy-3-methoxy-1-nitrobenzene. The second coupling partner 5-nitro-vanillic acid pure is synthesized from vanillic acid by nitration with 65% nitric acid followed by re-crystallization of the crude 5-nitro-vanillic acid intermediate from acetic acid. The convergent assembly of the oxadiazole moiety in 5-[3-(2,5-dichloro-4,6-dimethyl-pyridin-3-yl)-[1,2,4]oxadiazol-5-yl]-2-hydroxy-3-methoxy-1-nitrobenzene is achieved by first activation of 5-nitro-vanillic acid as its acid chloride and subsequent coupling with the aldoxime (Z)-2,5-dichloro-N'-hydroxy-4,6-dimethylnicotinimidamide. Cyclisation of the initially formed coupling product is achieved thermally to give the oxadiazole moiety by elimination of water. The reaction mixture of 5-[3-(2,5-dichloro-4,6-dimethyl-pyridin-3-yl)-[1,2,4]oxadiazol-5-yl]-2-hydroxy-3-methoxy-1-nitrobenzene, after ring closure reaction, is concentrated and product isolated from 1,4-dioxane/ethanol mixture in one step. Oxidation of the pyridine ring to the corresponding aryl-N-oxide (5-[3-(2,5-dichloro-4,6-dimethyl-1-oxy-pyridin-3-yl)-[1,2,4]oxadiazol-5-yl]-2-hydroxy-3-methoxy-1-nitrobenzene) is achieved with trifluoroperoxoacetic acid which is formed in situ from UHP (Urea hydrogen peroxide complex) and trifluoroacetic acid anhydride. Unreacted 5-[3-(2,5-dichloro-4,6-dimethyl-pyridin-3-yl)-[1,2,4]oxadiazol-5-yl]-2-hydroxy-3-methoxy-1-nitrobenzene is subsequently removed from 5-[3-(2,5-dichloro-4,6-dimethyl-1-oxy-pyridin-3-yl)-[1,2,4]oxadiazol-5-yl]-2-hydroxy-3-methoxy-1-nitrobenzene by repeated re-crystallisation from formic acid/toluene. The analogue intermediate 5-[3-(2,5-dichloro-4,6-dimethyl-1-oxy-pyridin-3-yl)-[1,2,4]oxadiazol-5-yl]-2-hydroxy-3-methoxy-1-nitrobenzene pure with a level of 5-[3-(2,5-dichloro-4,6-dimethyl-pyridin-3-yl)-[1,2,4]oxadiazol-5-yl]-2-hydroxy-3-methoxy-1-nitrobenzene below 0.10% area is converted to 5-[3-(2,5-dichloro-4,6-dimethyl-1-oxy-pyridin-3-yl)-[1,2,4]oxadiazol-5-yl]-3-nitrobenzene-1,2-diol crude analogue by ether cleavage in the presence of a stoichiometric amount of aluminium chloride and pyridine. After completion of the reaction, the crude product is isolated by precipitation with an aqueous hydrochloric acid followed by dissolution of the precipitate in formic acid. After polish filtration of the resulting solution and partial solvent switch from formic acid to isopropanol, 5-[3-(2,5-dichloro-4,6-dimethyl-1-oxy-pyridin-3-yl)-[1,2,4]oxadiazol-5-yl]-3-nitrobenzene-1,2-diol is crystallized from the resulting formic acid/IPA crystallization matrix and finally optionally milled to the desired particle size.

The invention claimed is:

1. A compound of the formula (I)

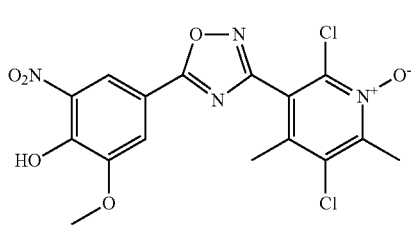

(I)

or a salt thereof.

2. A compound as claimed in claim 1 in crystalline form.

3. A compound as claimed in claim 1 in an organic solvent.

4. A compound as claimed in claims 3 wherein the organic solvent is N-methyl pyrrolidone.

5. A method of preparing a compound of the formula (II)

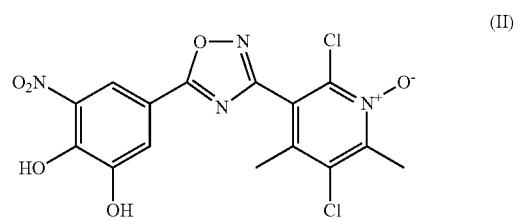 [SMILES: Cc1c(Cl)c(C)[n+]([O-])c(Cl)c1-c1noc(-c2cc(O)c(O)c([N+](=O)[O-])c2)n1]

(II)

or a salt thereof which comprises O-demethylation of a compound of the formula (I) as set forth in claim 1 or a salt thereof.

6. A method as claimed in claim 5 wherein the demethylation is effected by reaction with a Lewis acid and a base.

7. A method as claimed in claim 6 wherein the demethylation is carried out in solution in N-methyl pyrrolidone.

8. A method as claimed in claim 5 performed at 45° C. to 70° C.

9. A method as claimed in claim 5 wherein the compound of formula (I) or salt thereof is prepared by the oxidation of a compound of formula (III)

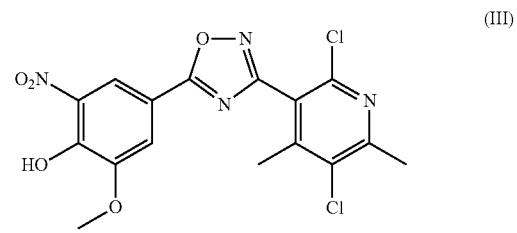 [SMILES: COc1cc(-c2nc(-c3c(Cl)nc(C)c(Cl)c3C)no2)cc([N+](=O)[O-])c1O]

(III)

or salt thereof.

10. A method as claimed in claim 9 wherein the oxidizing agent is $H_2O_2$.

11. A method as claimed in claim 10 wherein the $H_2O_2$ is $H_2O_2$-urea addition complex.

12. A method as claimed in claim 10 carried out in solution in methylene chloride to the presence of trifluoroacetic anhydride.

13. A method as claimed in claim 9 wherein the compound of the formula (III) is prepared by the reaction of the compound of formula (IV)

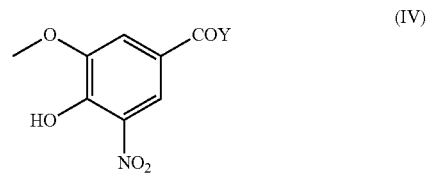

(IV)

wherein Y is a halo group or OR, in which R is hydrogen or a C1-C6 alkyl, with a compound of formula (V)

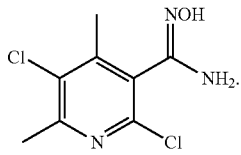

14. A method as claimed in claim 13 wherein Y is chloro and the compound of the formula (IV) has the formula (VIII):

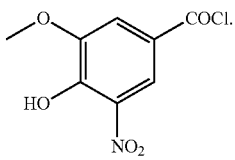

15. A method as claimed in claim 13 wherein Y is OR and R is hydrogen and the compound of formula (IV) has formula (VI):

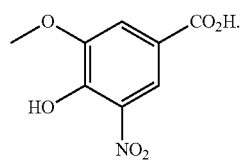

16. A method as claimed in claim 15, wherein the reaction includes the addition of a coupling reagent.

17. A method as claimed in claim 13 wherein the reaction of the compounds of formula (V) and formula (IV) takes place in a mixture of dimethylacetamide, tetrahydrofuran pyridine, or in dioxane in presence of pyridine.

18. A method as claimed in claim 17 wherein the reaction is performed at a temperature of 100° C. to 120° C.

19. A method as claimed in claim 13 wherein, following reaction of the compounds of formula (IV) and formula (V), ethanol is added to the mixture.

20. A method as claimed in claim 9 wherein the compound of formula (III) is oxidized to the compound of formula (I) without isolation or purification following the reaction of compounds of formula (IV) and formula (V).

21. A method as claimed in claim 9 wherein the compound of formula (I) is crystallised from an organic solvent.

22. A method as claimed in claim 21 wherein the organic solvent is a mixture of toluene and formic acid.

23. A method as claimed in claim 9 wherein the compound of formula (II) is crystallised from an organic solvent.

24. A method as claimed in claim 23 wherein the solvent is a mixture of propan-2-ol and formic acid.

25. A method as claimed in claim 9 wherein the compound of formula (VIII) is prepared from the compound of the formula (VI)

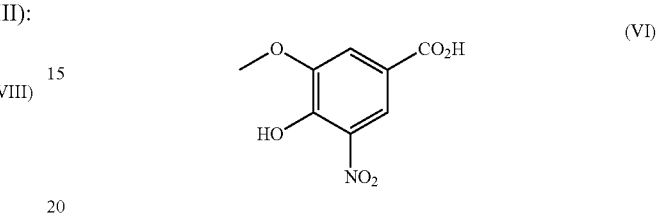

by reaction with $SOCl_2$ in dioxane at 75° C. to 85° C. or with $SOCl_2$ in DCM with DMF as catalyst.

26. A method as claimed in claim 25 wherein the compound of formula (VI) was prepared by the nitration of vanillic acid with 65% $HNO_3$ in acetic acid or by the nitration of methyl vanillate with 65% $HNO_3$ in dioxane/water, followed by the hydrolysis with sodium hydroxide.

27. A method as claimed in claim 9 wherein the compound of formula (V) is prepared from the compound of the formula (VII)

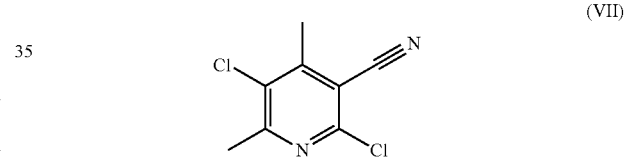

by reaction with hydroxylamine in the presence of 1,10-phenanthroline monohydrate.

28. A method as claimed in claim 27 wherein the reaction is carried in a mixture of methanol and water at 70-80° C.

29. A method as claimed in claim 6 wherein the demethylation is effected by reaction with aluminium chloride and pyridine.

30. A method as claimed in claim 13 wherein Y is chloro or OR, in which R is hydrogen, methyl or ethyl.

* * * * *

UNITED STATES PATENT AND TRADEMARK OFFICE
CERTIFICATE OF CORRECTION

PATENT NO. : 9,126,988 B2  
APPLICATION NO. : 14/365265  
DATED : September 8, 2015  
INVENTOR(S) : Domenico Russo et al.

Page 1 of 1

It is certified that error appears in the above-identified patent and that said Letters Patent is hereby corrected as shown below:

On the Title Page

Item (71), change Applicant name from "BIAL-PORTELA & CA, S.A." to -- BIAL-PORTELA & CA., S.A. --;

Item (73), change Assignee name from "BIAL-PORTELA & CA, S.A." to -- BIAL-PORTELA & CA., S.A. --.

Signed and Sealed this
Twenty-seventh Day of February, 2024

Katherine Kelly Vidal
*Director of the United States Patent and Trademark Office*